March 25, 1947. C. MALLERIN Plant Pat. 729
ROSE PLANT
Filed Jan. 25, 1944
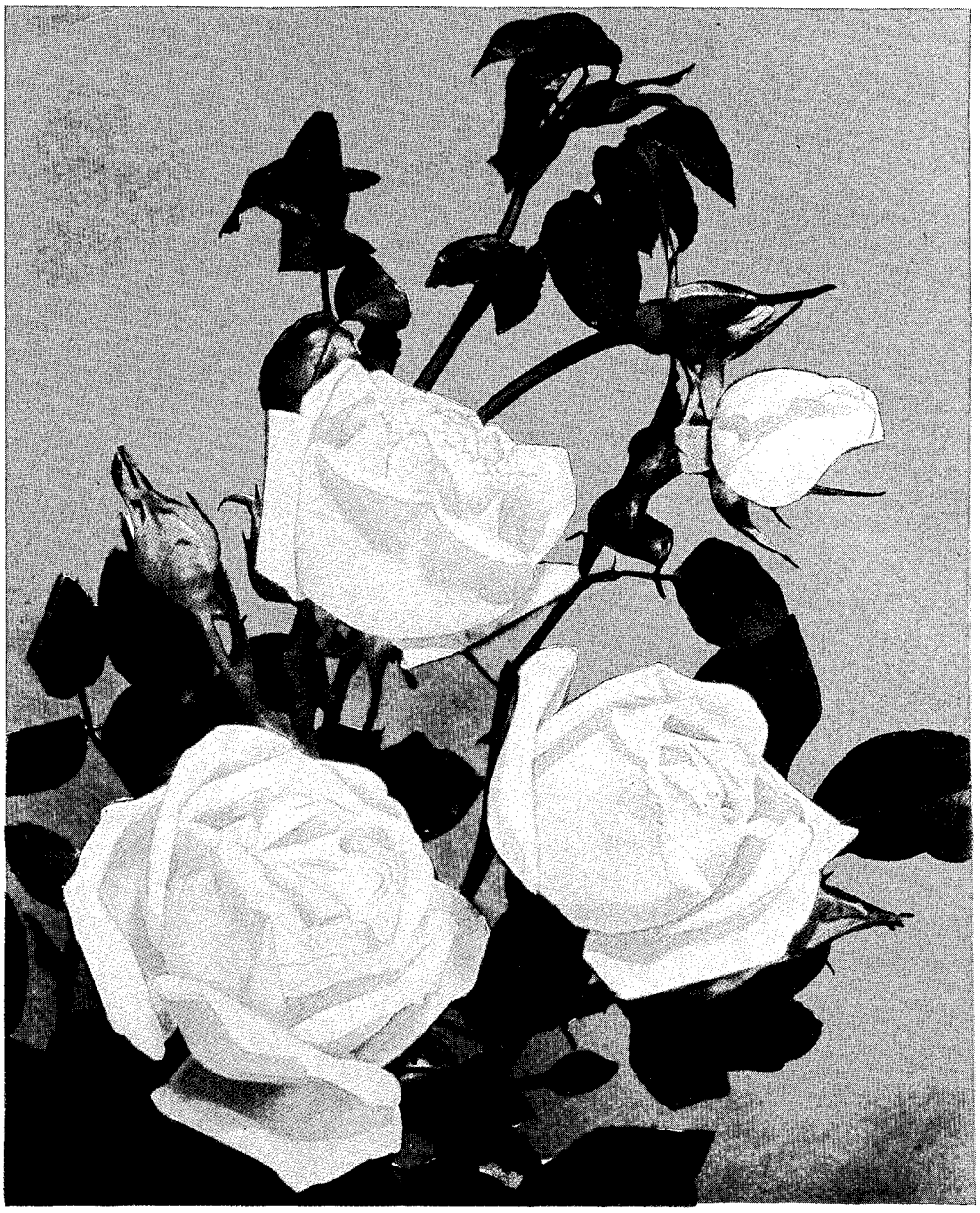
Inventor
Charles Mallerin
By Robb & Robb
Attorneys Patented Mar. 25, 1947

Plant Pat. 729

UNITED STATES PATENT OFFICE

729

ROSE PLANT

Charles Mallerin, Varces, France, assignor to The Conard-Pyle Company, West Grove, Pa., a corporation of Pennsylvania Application January 25, 1944, Serial No. 519,693

1 Claim. (Cl. 47—61)

The present invention relates to a new and distinct variety of hybrid tea rose plant resulting from the crossing of "McGredy's Ivory" and an unnamed seedling and marking an important improvement in the field of roses.

This new variety is characterized as to novelty by the fine qualities of its primary characteristics, in comparison with its parents or any other rose in its class. More specifically, these characteristics comprise in combination, vigor of habit, shiny or glossy foliage with high resistance to disease, and free habit of blooming, with long lasting flowers of brilliant yellow color that fade less than most yellows and hold their yellow color even in the bright sunshine. This rose has an unusually fine fragrance.

Asexual reproduction of this new variety shows the foregoing characteristics come true to form and are established.

The following is a detail description of the new variety, color terminology being in accord with Ridgway's Color Standard:

Type: Hardy; bush; seedling; for cut flowers and garden decoration.
Class: Hybrid tea.
Breeding: Seedling.
*Seed parent.*—"McGredy's Ivory."
*Pollen parent.*—Unnamed seedling.
Propagation: Holds its distinguishing characteristics through succeeding propagations by budding, which is the only method employed up to the present time.

*Flower*

Locality where grown: West Grove, Pennsylvania.
Flowers borne: Singly; two to three to stem; in regular cluster; on strong, medium length stems.
Quantity of bloom: Free; outdoors.
Continuity: Intermittent.
Fragrance: Tea.
Bud:
*Peduncle.*—Medium long; medium heavy; erect; stiff; Bordeaux, Plate XII; entirely smooth.
*Before calyx breaks.*—Size—large. Form—ovoid with a conspicuous neck; with foliaceous appendages on the surface of the bud; with bristle-like foliaceous parts extending beyond the tip of the bud equal to one-half or more of its length.
*As calyx breaks.*—Color—Light Cadmium, Plate IV, blotched with Carmine, Plate I.

*As first petal opens.*—Size—large. Form—ovoid. Color—outside: Light Cadmium, Plate IV, blotched with Carmine, Plate I; inside—Lemon Yellow, Plate IV.
*Opening.*—Opens up well.
Bloom:
*Size.*—When fully open—large; 4½ inches to 4¾ inches.
*Petalage.*—Very double; from 45 to 50 petals, arranged regularly.
*Form.*—Cupped; becoming high centered, globular; petals remaining at first loosely rolled inward; becoming later, at maturity, loosely rolled inward.
Petals: Thick; with inside and outside satiny.
*Shape.* — Outside — obovate; intermediate—obovate; inside—obovate.

This description of a newly opened flower was made from a rose grown outdoors in the month of October, 1943, at West Grove, Pennsylvania:

*Color—Outside petal*—outside surface: Mustard Yellow, Plate XVI, lightly tinted Carmine, Plate I; inside surface: Amber Yellow, Plate XVI. *Intermediate petal*—outside surface: Mustard Yellow, Plate XVI; inside surface: Amber Yellow, Plate XVI. *Inner petal*—outside surface: Empire Yellow, Plate IV; inside surface: Lemon Chrome, Plate IV.

This description was made from a rose that was open for three days outdoors, in the month of October, 1943, at West Grove, Pennsylvania:

*Color. — Outside petal* — outside surface: Straw Yellow, Plate XVI; inside surface: Naphthalene Yellow, Plate XVI. *Inside petal*—outside surface: Massicot Yellow, Plate XVI; inside surface: Massicot Yellow, Plate XVI.
*General color effect.*—Newly opened flower—Wax Yellow, Plate XVI. Three days open—Massicot Yellow, Plate XVI.
*Behavior.*—Crop off cleanly.
*Flower longevity.*—On bush in garden 3 to 4 days in October. Cut roses grown outdoors and kept at living room temperatures, 4 to 5 days in October.

*Reproductive organs*

Stamens: Many; arranged irregularly about pistils.
Filaments: Long; Wax Yellow, Plate XVI; most with anthers.

Anthers: Medium size; Primuline Yellow, Plate XVI.
Pollen: Moderate; Empire Yellow, Plate IV.
Pistils: Few.
Styles: Uneven; medium long; medium heavy; bunched.
Stigma; Picric Yellow, Plate IV.
Ovaries: All enclosed in calyx.
Hips: Globular; Parrot Green, Plate VI; with inconspicuous neck; smooth; walls thick, fleshy.
Sepals: Permanent; moderately long; spear-shaped; recurved.
Seeds: Few; medium large.

*Plant*

Foliage:

*Leaves.*—Compound of three to five leaffets; normally abundant; moderately large; leathery; glossy; wrinkled.

*Leaflets.*—Shape—lanceolate with apex acute. Base—round. Margin—simply serrate.

*Color.*—*Mature*—upper surface: Dusky Olive Green, Plate XLI; under surface: Garnet Brown, Plate I. *Young*—upper surface: Olive Green, Plate IV, suffused Garnet Brown, Plate I; under surface: Garnet Brown, Plate I.

*Rachis (the supporting stem of the compound leaf.)*—Heavy. Upper side—smooth; grooved; under side—sparsely prickly.

*Stipules.*—Medium length; wide; with medium long points, turning out at an angle of less than 45°.

*Disease.*—Resistant.

Growth:

*Habit.*—Bushy; upright.

*Growth.*—Moderate.

*Canes.*—Medium heavy.

*Main stems* — Grass Green, Plate VI. *Thorns*—few; short; hooked downward; with broad round base. *Prickles*—none. *Hairs*—none.

*Branches.*—Dull; Grass Green, Plate VI. *Thorns*—few; short; hooked downward; with broad round base. *Prickles*—none. *Hairs*—none.

*New shoots.*—Dull; Oxblood Red, Plate I. *Thorns* — none. *Hairs* — none. *Prickles*—none.

I claim:

A new and distinct variety of hybrid tea rose plant, characterized as to novelty by its vigor of habit, glossy foliage with high resistance to disease, free habit of blooming, long lasting quality of blooms, the brilliant yellow color of flowers and persistence of such color in bright sunlight, and fine fragrance, substantially as shown and described.

CHARLES MALLERIN.